United States Patent
Chung et al.

(10) Patent No.: US 10,531,804 B2
(45) Date of Patent: Jan. 14, 2020

(54) **METHOD FOR ACQUIRING T2\* AND VASCULAR IMAGES FROM MAGNETIC RESONANCE IMAGING SYSTEM**

(71) Applicants: GACHON UNIVERSITY OF INDUSTRY-ACADEMIC COOPERATION FOUNDATION, Seongnam-si (KR); GIL MEDICAL CENTER, Incheon (KR)

(72) Inventors: Jun Young Chung, Incheon (KR); Eung Yeop Kim, Incheon (KR)

(73) Assignees: GACHON UNIVERSITY OF INDUSTRY-ACADEMIC COOPERATION FOUNDATION, Seongnam-si (KR); GIL MEDICAL CENTER, Incheon (KR)

( * ) Notice: Subject to any disclaimer, the term of this patent is extended or adjusted under 35 U.S.C. 154(b) by 413 days.

(21) Appl. No.: 15/319,154

(22) PCT Filed: Mar. 26, 2015

(86) PCT No.: PCT/KR2015/002984
§ 371 (c)(1),
(2) Date: Dec. 15, 2016

(87) PCT Pub. No.: WO2015/194743
PCT Pub. Date: Dec. 23, 2015

(65) Prior Publication Data
US 2017/0135589 A1 May 18, 2017

(30) Foreign Application Priority Data

Jun. 18, 2014 (KR) .................. 10-2014-0074442

(51) Int. Cl.
*A61B 5/026* (2006.01)
*G01R 33/50* (2006.01)
(Continued)

(52) U.S. Cl.
CPC ............ *A61B 5/0263* (2013.01); *A61B 5/055* (2013.01); *G01R 33/50* (2013.01);
(Continued)

(58) Field of Classification Search
CPC ...... A61B 5/0263; A61B 5/055; G01R 33/00; G01R 33/50; G01R 33/5635; G01R 33/56509
See application file for complete search history.

(56) References Cited

U.S. PATENT DOCUMENTS 5,810,727 A * 9/1998 Groen .............. G01R 33/56308
324/307
2009/0251140 A1 * 10/2009 Bhardwaj .......... G01R 33/5615
324/307

(Continued)

FOREIGN PATENT DOCUMENTS

JP 7-67855 A 3/1995
JP 7-184879 A 7/1995
(Continued)

OTHER PUBLICATIONS

Markl, Michael. "Gradient Echo Imaging" Journal of Magnetic Resonance Imaging 35:1274-1289 (2012) (Year: 2012).*
(Continued)

*Primary Examiner* — Tse W Chen
*Assistant Examiner* — Milton Truong
(74) *Attorney, Agent, or Firm* — Seed IP Law Group LLP (57) ABSTRACT

According to the present invention, accurate T2* and vascular images are concurrently acquired by acquiring a T2* image without a flow compensation and a T2* image with a flow compensation and subtracting the two images to reconstitute an image showing the flow phenomenon. Furthermore, an accurate T2* image can be acquired by using the readout gradient without the flow compensation and also the (Continued)

accurate T2* and vascular images can be concurrently acquired. The clinical judgment for blood flow rate of the blood vessel and the clinical judgment for acute stroke can be concurrently made, and so the present invention can be widely utilized in clinical practice.

10 Claims, 10 Drawing Sheets (51) Int. Cl.
*A61B 5/055* (2006.01)
*G01R 33/563* (2006.01)
*G06T 5/50* (2006.01)

(52) U.S. Cl.
CPC ............ *G01R 33/5635* (2013.01); *G06T 5/50* (2013.01); *G06T 2207/30101* (2013.01)

(56) References Cited

U.S. PATENT DOCUMENTS

2010/0160767 A1* 6/2010 Deimling ........... G01R 33/5613 600/419
2010/0280357 A1 11/2010 Bi et al.
2011/0275926 A1* 11/2011 Du ..................... G01R 33/5635 600/410
2012/0046541 A1 2/2012 Wheaton
2014/0114177 A1 4/2014 Chen et al.

FOREIGN PATENT DOCUMENTS

| JP | 2009-125582 A | 6/2009 |
| JP | 2011-143241 A | 7/2011 |
| JP | 2011-254905 A | 12/2011 |
| KR | 10-2004-0032064 A | 5/2006 |
| WO | 2011/034004 A1 | 3/2011 |

OTHER PUBLICATIONS

Markl, Michael. "Velocity Encoding and Flow Imaging", http://ee-classes.usc.edu/ee591/library/Markl-FlowImaging.pdf, Online since Dec. 28, 2013 (Year: 2013).*

* cited by examiner

【Fig. 1】

FIG. 2(a) VEIN

FIG. 2(b) ARTERY

FIG. 2(c) VEIN & ARTERY

Modified Sequence TE = 15, TR = 630, With FC

Modified Sequence TE = 15, TR = 630, Without FC

METHOD FOR ACQUIRING T2* AND VASCULAR IMAGES FROM MAGNETIC RESONANCE IMAGING SYSTEM

TECHNICAL FIELD

The present invention relates to an imaging technique implemented by an MRI (Magnetic Resonance imaging) system, and more specifically to an imaging technique capable concurrently acquiring T2* and vascular images from an MRI system.

BACKGROUND ART

Diagnostic imaging methods include devices utilizing a variety of techniques such as X-ray, CT, ultrasonic, RI imaging, or MRI. Among them, MRI is the least harmful to the human body as compared with the other diagnostic imaging methods and forms images of the constituents in the human body. Hence, MRI is a very important device in clinical practice.

MRI devices can obtain tissue parameters such as spin density, T1, T2, chemical shift, magnetic transition, chemical exchange saturation transfer, blood flow, or spectroscopy, which are unique information of the living body. Various biometric information images can also be obtained through such parameters.

Magnetic Resonance Angiography (MRA) is a method for measuring a blood flow in the arteries and veins of the human body using the MRI device and reconstituting the measured blood flow as an image. The MRA is currently providing clinical information which is very important for the diagnosis and treatment of vascular diseases. In the case of MRA imaging, there are various methods that utilize the properties of the blood flow rate, (i.e., TOF (time of flight)), using T1-weighted imaging of the blood flow.

Figure 1:
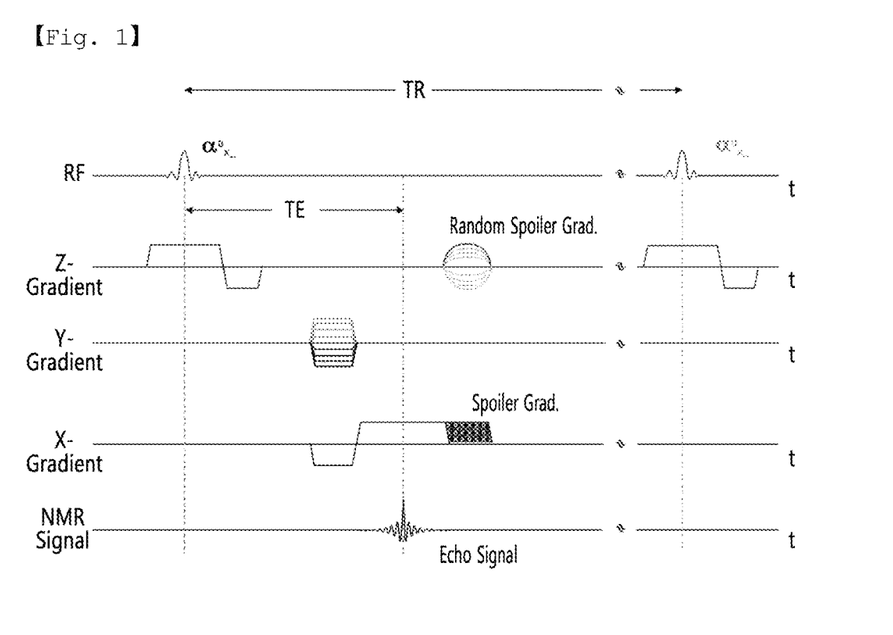
FIG. 1 represents a pulse sequence of FLASH (Fast Low Angle Shot) used to obtain a conventional MRA imaging.
Figure 2A:
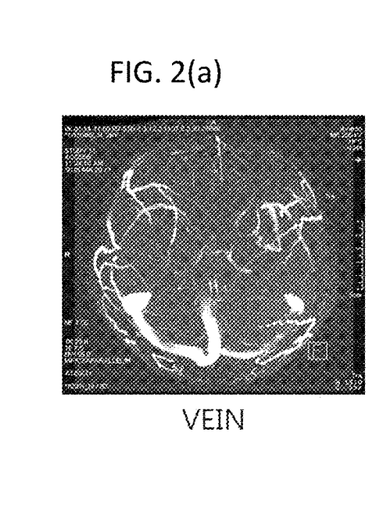
FIGS. 2(a) to 2(c) represent the images acquired using pulse sequences of FLASH and show images of vein, artery and vein & artery, respectively.
Figure 2B:
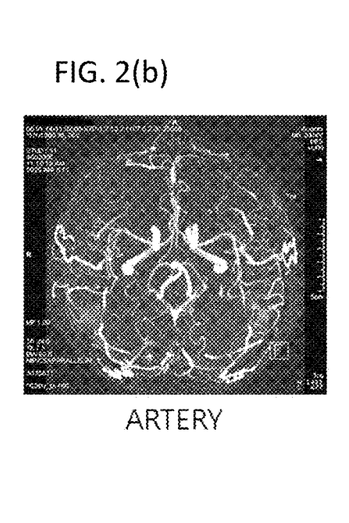
Figure 2C:
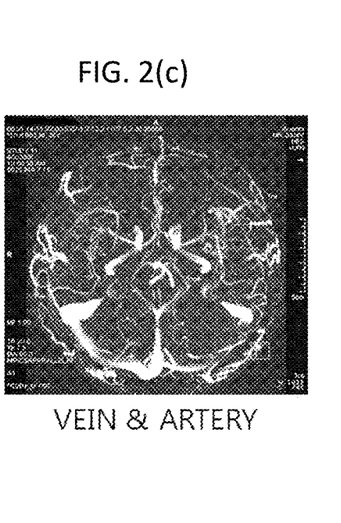

FIG. 1 represents a pulse sequence of FLASH (Fast Low Angle Shot) used to obtain a conventional MRA image. FIGS. 2a to 2c represent images acquired using a FLASH pulse sequence, which show images of an artery, vein, and artery & vein.

FLASH techniques have advantages such as a rapid image acquisition speed, short TE (echo time) and TR (repetition time), and low flip angle, but they have disadvantages as compared with spin echo imaging techniques; for example, the contrast of the tissue is lower, many artifacts are generated, and the signal-to-noise ratio (SNR) is low.

Further, T2* relaxation represents a traverse attenuation produced due to an irregularity of the external magnetic field, together with T2 relaxation by the impact between the spindles. T2* weighted images are very useful in clinical judgments which observe the degree of oxidation of the iron component due to a cerebral hemorrhage.

Such imaging techniques are useful to diagnose cerebrovascular diseases, which are second only to cancer as the ranking cause of death of Korean people, but there is a problem in that is necessary to go through for the acquisition process for each individual image. Diagnosis of acute stroke should be made promptly. This is because, the greater the time delay, the more exponentially brain cells undergo irreversible changes. Therefore, it is necessary to minimize the image acquisition time. If an acute stroke is suspected, imaging techniques that are undergone first are T2*GRE. If the blood brain condition can be judged by utilizing this imaging technique, the time taken to obtain TOF MRA can be shortened.

DISCLOSURE OF INVENTION

Technical Problem

The present invention has been conceived in accordance with the above-described technical background, and an object of the invention is to provide a method capable of concurrently acquiring accurate T2* and vascular images from a magnetic resonance imaging (MRI) system.

Another object of the present invention is to provide a method capable of concurrently acquiring accurate T2* and vascular images from the magnetic resonance imaging system, thereby shortening the total image acquisition time and obtaining the sufficient image quality.

Technical Solution to Problem

In order to achieve the above-described objects, accurate T2* and vascular images are concurrently acquired by acquiring a T2* image without a flow compensation and a T2* image with a flow compensation, and subtracting the two images to further reconstitute an image showing the flow phenomenon.

Another object of the present invention is to provide a method for concurrently acquiring T2* and vascular images from a magnetic resonance imaging (MRI) system, the method comprising: repeating processes of alternatively applying a first readout gradient which acquires a T2* weighted image without a flow compensation and a second readout gradient which acquires a T2* weighted image with a flow compensation, with a desired resolution of image, to acquire a signal; reconstituting the acquired signal to form two images that reflect different flow phenomenon from each other; and subtracting, from one of the two images, another image to acquire a difference image.

In the present invention, it is preferable that an echo time (TE) of applying the first and second readout gradients is more than 15 msec.

The first readout gradient can be applied in a negative direction and then applied in the positive direction to be two times the area of the gradient applied in the negative direction. The second readout gradient can be applied in a positive direction in a constant amount, applied two times in a negative direction in the constant amount, and then applied in the positive direction as much the amount of area of two times the constant amount.

The two images that reflect different flow phenomenon from each other are the minimized flow phenomenon image and the weighted flow phenomenon image which are acquired using the first and second readout gradients, respectively. It is possible to output the minimized flow phenomenon image and the difference image or MIP (Maximum Intensity Projection) image of the subtraction image as the result.

It is preferable that a constant interval not applied by the readout gradient is comprised between the application of the first readout gradient and the application of the second readout gradient.

The method of the present invention may further comprise the step of performing MIP (Maximum Intensity Projection) on the subtraction image to reconstitute a vascular image.

Advantageous Effects of the Invention

When both T2* and vascular images are concurrently acquired using the pulse sequence according to one embodiment of the present invention, accurate T2* image can be acquired by using the readout gradient without the flow compensation and also accurate T2* and vascular images can be concurrently acquired. Therefore, the clinical judgment for blood flow rate of the blood vessel and the clinical judgment for acute stroke can be concurrently made, and so the present invention can be widely utilized in clinical practice.

Furthermore, the method for concurrently acquiring T2* and vascular images according to one embodiment of the present invention can ensure a quality of images which is comparable with that of images obtained by established protocols, and can shorten the total image acquisition time by 40% as compared with the case of sequentially acquiring traditional T2* weighted and MRA images, As such, the present invention has the advantages reducing a burden on patients when clinically applied. Particularly, this is thought to be very useful in the case of acute ischemic stroke patients.

DETAILED DESCRIPTION FOR CARRYING OUT THE INVENTION

Hereinafter, preferred embodiments of the method for acquiring images through the magnetic resonance imaging system according to the present invention are described in detail with reference to the attached drawings. However, description concerning well-known functions and configurations which can make the subject matter of the present invention unnecessarily vague will be omitted.

The configurations of the MRI system as applied to the present invention are widely known in the art and so the description thereof is omitted.

Figure 3:
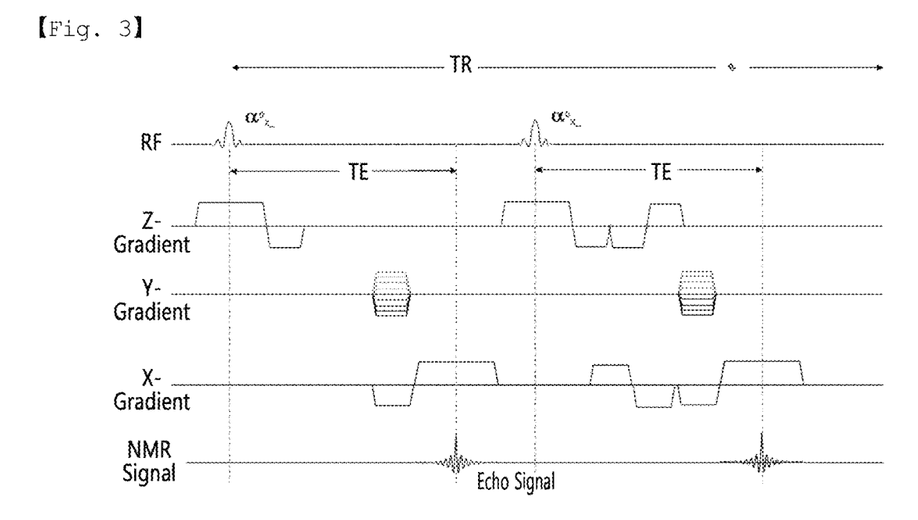
FIG. 3 represents the pulse sequences used in the method concurrently acquiring T2* and vascular images according to an embodiment of the present invention.

FIG. 3 represents the pulse sequences used in the method for concurrently acquiring T2* and vascular images according to an embodiment of the present invention.

In FIG. 3, Z-gradient, Y-gradient and X-gradient represent a slice selection, a phase decoding and a readout gradient, respectively.

As shown in FIG. 3, the readout gradient without a flow compensation is applied in a negative direction and then applied in a positive direction so as to be two times the area of the gradient applied in the negative direction.

Further, the readout gradient with a flow compensation is not applied for a certain time within echo time (TE), then applied in a positive direction, applied in a negative direction, again applied in a negative direction and then again applied in a positive direction. The amount of area of the readout gradients thus applied is (1, −1, −1, 2) when the amount of area of the readout gradient applied first is 1.

The signal acquired by the readout gradient without a flow compensation and the signal acquired by the readout gradient with a flow compensation are repeatedly acquired with a desired resolution of images to reconstitute the images, thereby acquiring two images that reflect different flow phenomenon from each other. The two images thus acquired are the minimized flow phenomenon first T2* image and the weighted flow phenomenon second T2* image.

By acquiring T2* image according to the increase and decrease of such flow phenomenon, one minimized flow phenomenon T2* image (first T2* image), and two acquired images (first and second T2* images) can be subtracted to further obtain a third image showing the blood flow part. Then, MIP on the third image is conducted to reconstitute the vascular image.

The images acquired through T2* and vascular images according to one embodiment of the present invention are a minimized flow phenomenon T2* image acquired using the readout gradient without a flow compensation, and a vascular image obtained from the subtraction between two T2* images. According to this method, the T2* image and the vascular image can be concurrently acquired from one scan and also a more accurate image can be obtained even with respect to the T2* image. These will be described later.

The embodiment of the present invention described with reference to FIG. 3 uses the pulse sequence in the form of first applying the readout gradient without a flow compensation, and then applying the readout gradient with a flow compensation. It does not matter if the order thereof is changed.

Figure 4:
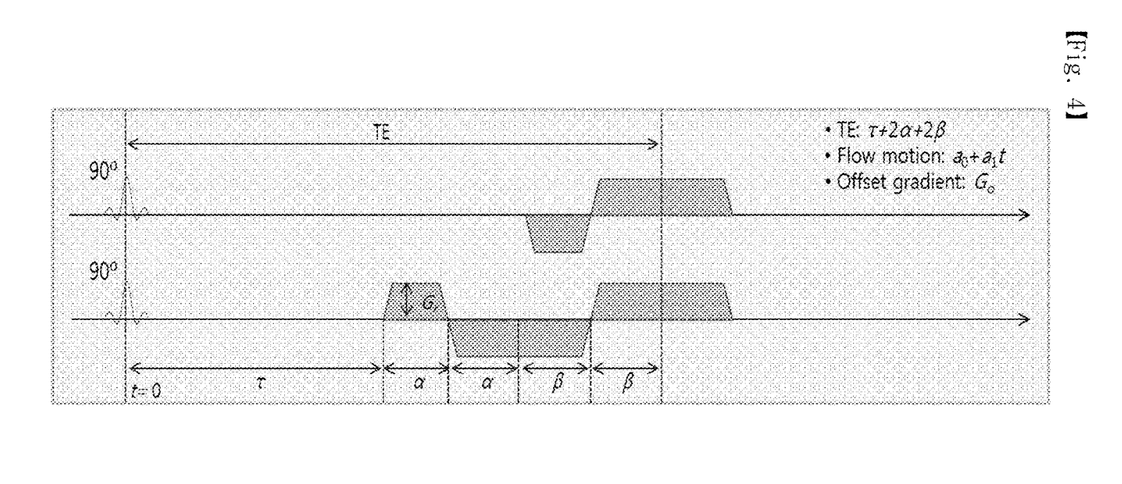
FIG. 4 is a view illustrating the theoretical background of the pulse sequences used in the method for concurrently acquiring T2* and vascular images according to an embodiment of the present invention.

FIG. 4 is a view illustrating the theoretical background of the pulse sequences used in the method for concurrently acquiring T2* and vascular images according to an embodiment of the present invention. In order to acquire the T2* image, TE time must be more than 15 msec. Given these circumstances, the modeling is made assuming offset gradient (Go). The formula must account for this.

As shown in FIG. 4, the entire echo time is configured as in the following equation (1):

$$TE = \tau + 2\alpha + 2\beta \quad \text{[Formula 1]}$$

The movement of the blood flow can be expressed as the following equation (2):

$$\text{Flow motion} = a_0 + a_1 t$$

wherein $a_0$ is a static component and does not influence the phase due to $G_r$ in t=TE. Hence, considering only the $a_1 t$ component is enough, and the phase disagreement due to an offset gradient ($G_0$) should be considered even at $a_0$ component. For the first compensation, $\alpha = \beta$.

The phase without a flow compensation is expressed as the following equation (3):

$$\phi = -\gamma \int_0^{\tau+2\alpha+2\beta} G_0 a_0 dt - \gamma \int_0^{\tau+2\alpha} G_0 a_1 t dt - \gamma \int_{\tau+2\alpha}^{\tau+2\alpha+\beta} \quad \text{[Formula 3]}$$

$$(G_0 - G_r) a_1 t dt - \gamma \int_{\tau+2\alpha+\beta}^{\tau+2\alpha+2\beta} (G_0 + G_r) a_1 t dt$$

$$= -\gamma \left[ G_0 a_0 (\tau + 2\alpha + 2\beta) + G_r a_1 \beta^2 - \frac{1}{2} G_0 a_1 (\tau + 2\alpha + 2\beta)^2 \right]$$

The ordinary vascular image acquired by weighting the T1 value of the blood usually uses a flow compensation, but the method according to the embodiment of the present invention does not use a flow compensation in acquiring the T2* image, through which it has been found that a more accurate T2* image can be acquired.

Meanwhile, the phase with a flow compensation is expressed as the following equation (4):

$$\phi = -\gamma \int_0^{\tau+2\alpha+2\beta} G_0 a_0 dt - \gamma \int_0^{\tau} G_0 a_1 t dt - \gamma \int_{\tau}^{\tau+\alpha} (G_0 + G_r) \quad \text{[Formula 4]}$$

$$a_1 t dt - \gamma \int_{\tau+\alpha}^{\tau+2\alpha+\beta} (G_0 - G_r) a_1 t dt - \gamma \int_{\tau+2\alpha+\beta}^{\tau+2\alpha+2\beta} (G_0 + G_r)$$

$$a_1 t dt$$

$$= -\gamma \left[ G_0 a_0 (\tau + 2\alpha + 2\beta) + G_r a_1 (\beta^2 - \alpha^2) - \frac{1}{2} G_0 a_1 \right.$$

$$\left. (\tau + 2\alpha + 2\beta)^2 \right]$$

Figure 5:
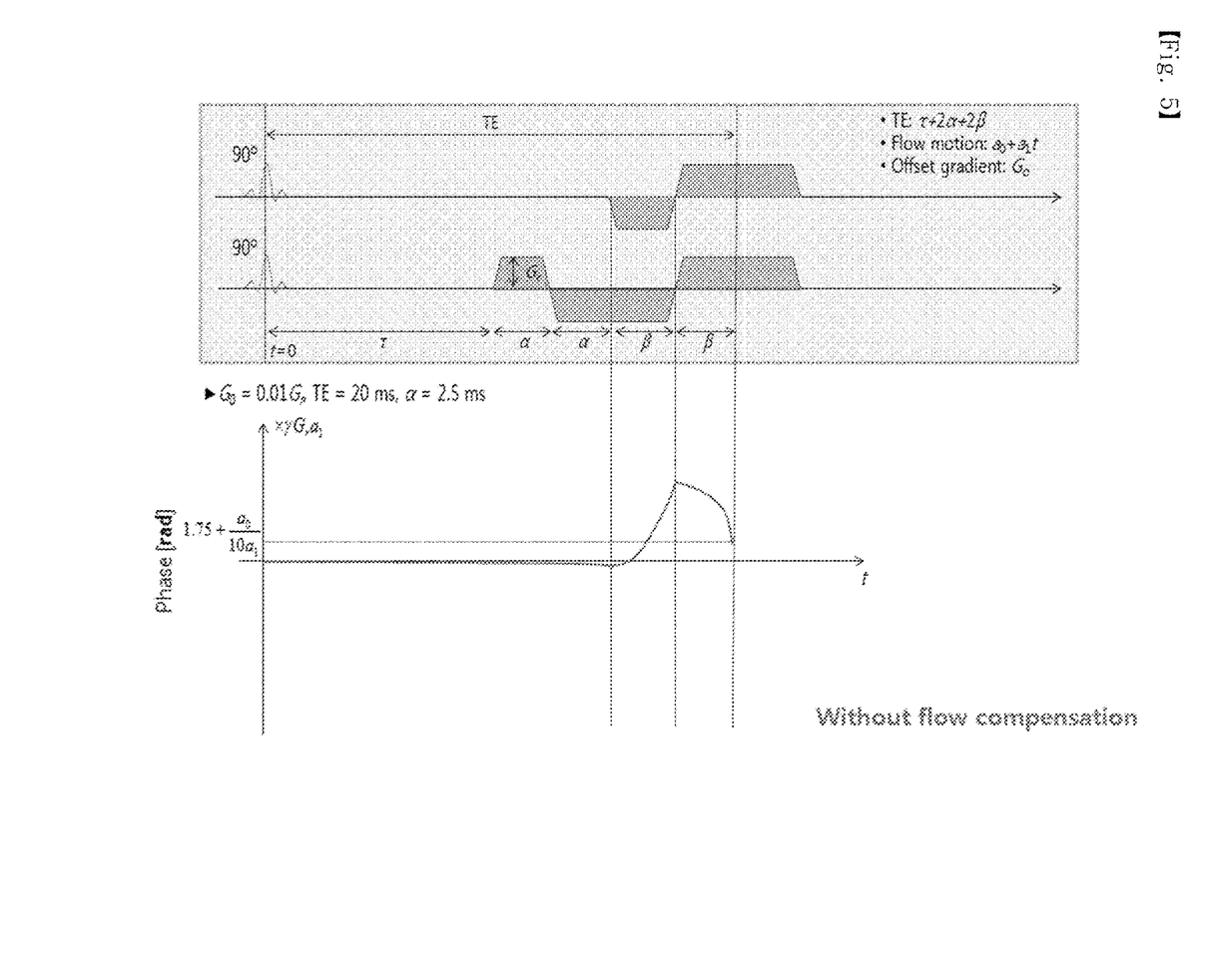
FIGS. 5 and 6 represent the phase without a flow compensation and the phase with a flow compensation, respectively, in the method for concurrently acquiring T2* and vascular images according to an embodiment of the present invention.
Figure 6:
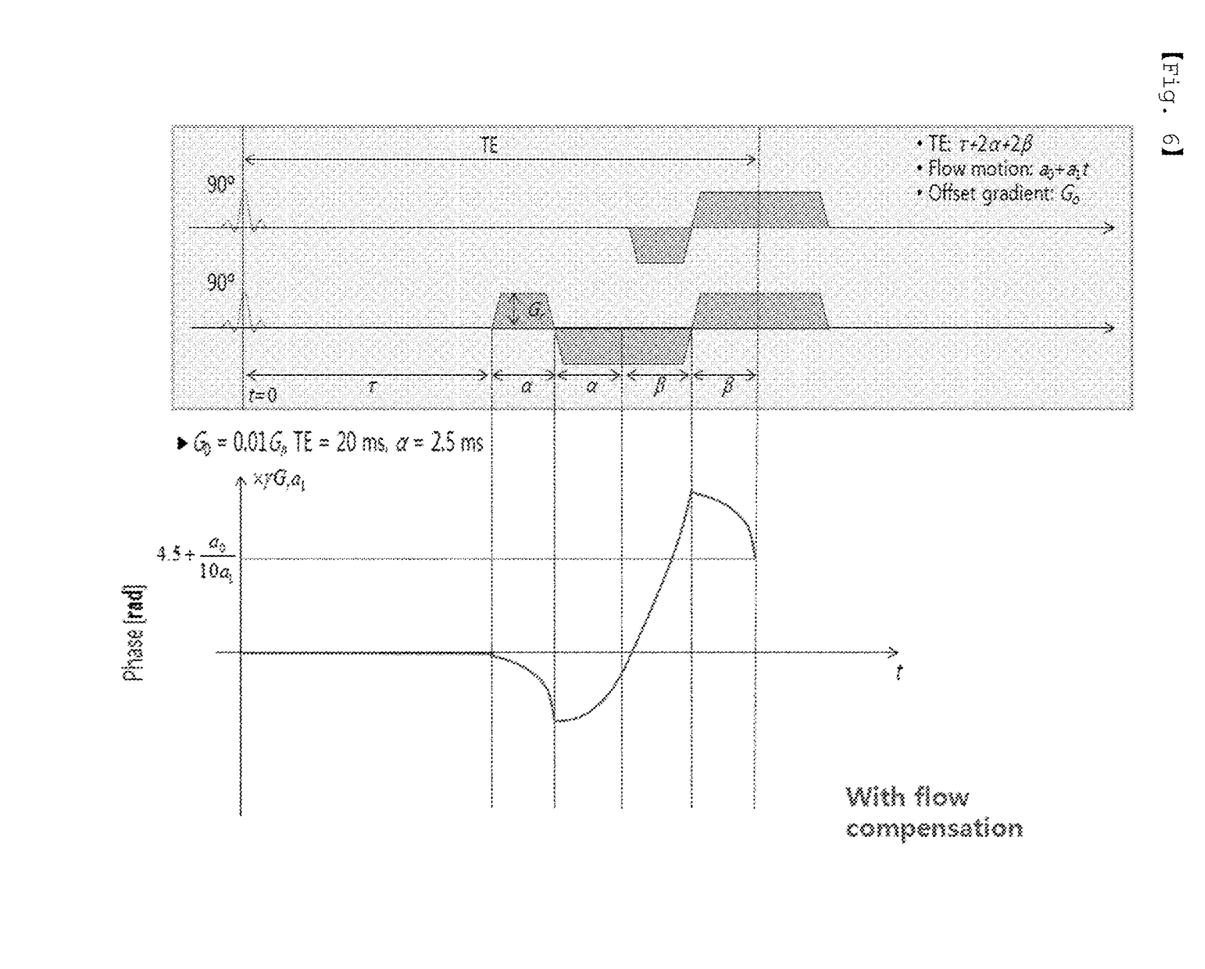
Figure 7A:
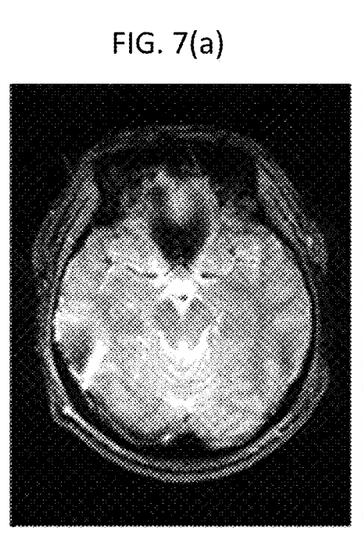
FIGS. 7(a)-7(c) and FIGS. 8(a)-8(c) represent the images acquired using pulse sequences according to an embodiment of the present invention, which show an image with a flow compensation and an image without a flow compensation, respectively.
Figure 7B:
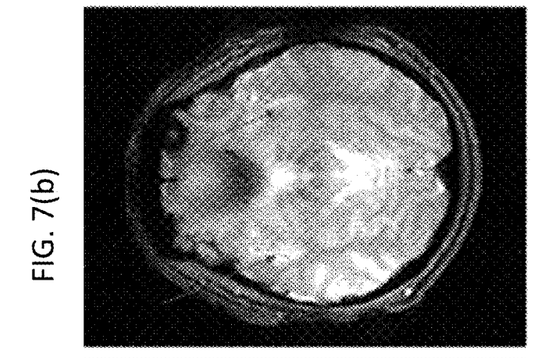
Figure 7C:
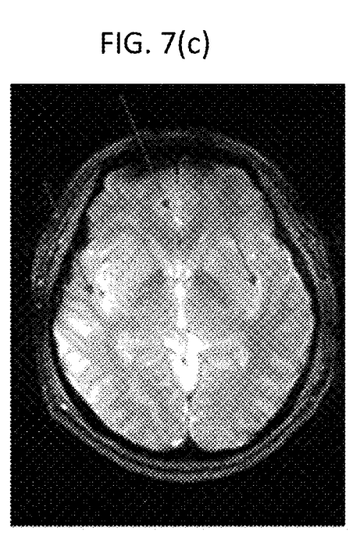
Figure 8A:
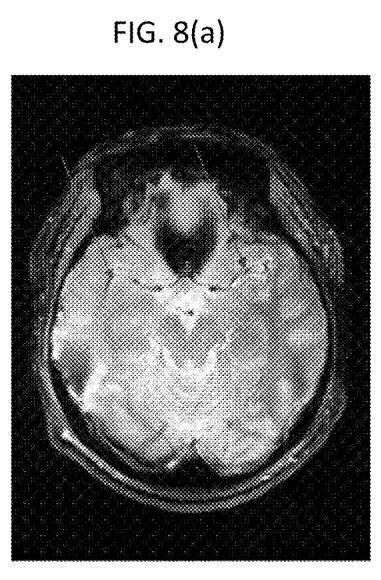
Figure 8B:
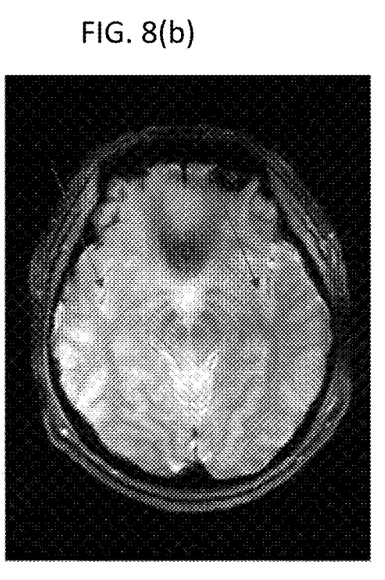
Figure 8C:
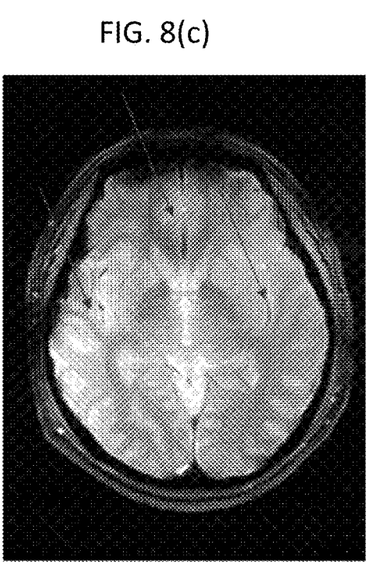

FIGS. 5 and 6 represent the phases without a flow compensation and with a flow compensation according to the equation above.

FIGS. 7(a)-7(c) and 8(a)-8(c) represent the images acquired using pulse sequences according to an embodiment of the present invention, which show an image with a flow compensation and an image without a flow compensation, respectively.

Figure 9A:
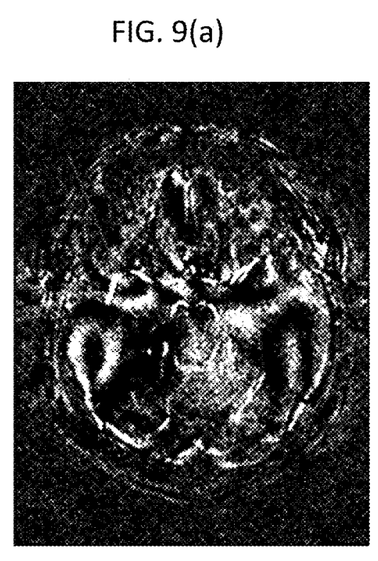
FIGS. 9(a)-9(c) represents images obtained from the subtraction of the images shown in FIGS. 7a-7(c) and FIGS. 8(a)-8(c).
Figure 9B:
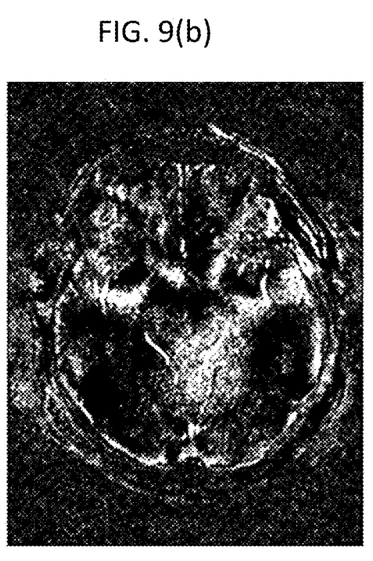
Figure 9C:
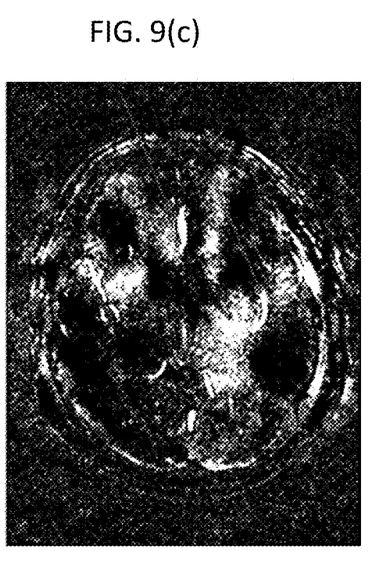
Figure 10A:
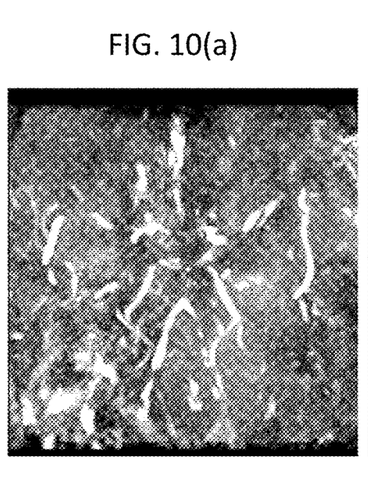
FIGS. 10(a)-10(c) shows MIP (Maximum Intensity Projection) images of the images shown in FIGS. 9(a)-9(c).
Figure 10B:
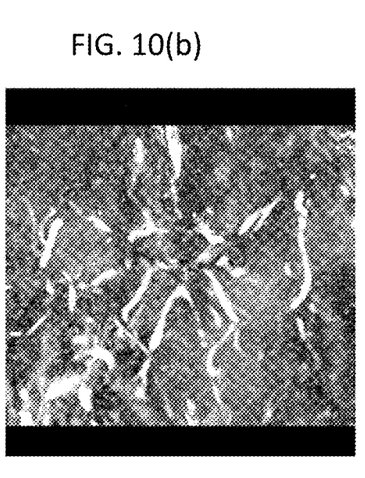
Figure 10C:
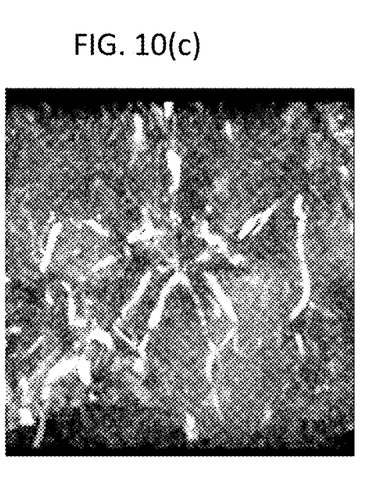

FIGS. 9(a)-9(c) represents images obtained from the subtraction of the images shown in FIGS. 7(a)-7(c) and FIGS. 8(a)-8(c). FIGS. 10(a)-10(c) shown MIP (Maximum Intensity Projection) imaging of the imaging shown in FIGS. 10(a)-10(c).

As shown in FIGS. 9 and 10, in the case of using the pulse sequence according to one embodiment of the present invention, accurate T2* and vascular imaging can be concurrently acquired. That is, the difference between the gradient with a flow compensation and the gradient without a flow compensation can be used to identify the flow phenomenon of the blood in the blood vessel. In the flow compensation method used for an ordinary vascular image which is acquired by weighing the T1 value of the blood, it has been analyzed and identified that, in the case of acquiring T2* images, it is useful to not perform a flow compensation in the acquisition of the more accurate image.

Using such an image, the clinical judgment for the blood flow rate of the blood vessel and the clinical judgment for acute stroke can be concurrently made, and so the present invention can be widely utilized in a clinical practice.

Furthermore, as shown in FIGS. 9(a)-9(c) and FIGS. 10(a)-10(c), the method for concurrently acquiring T2* and vascular images according to one embodiment of the present invention can ensure the quality of image which is comparable with that of images obtained by established protocols, and shorten the total acquisition time by 40% as compared with the case of sequentially acquiring traditional T2* weighted image and MRA images.

Although the forgoing is described with reference to the preferred embodiments of the present invention, it will be appreciated by those of ordinary skill that various changes and modifications can be made to the present invention without departing from the sprit and scope of the invention as set forth in the claims below.

What is claimed is:

1. A method for producing at least one T2* weighted image and a vascular image from a magnetic resonance imaging (MRI) system, the method comprising:
    performing a scan with the MRI system including repeatedly alternatively using a first readout gradient which corresponds with a T2* weighted image without a flow compensation and a second readout gradient which corresponds with a T2* weighted image with a flow compensation, with a desired resolution of image, to acquire a signal;
    reconstituting the signal to produce the T2* weighted image without a flow compensation and the T2* weighted image with a flow compensation;
    subtracting, the T2* weighted image without a flow compensation from the T2* weighted image with a flow compensation, or the T2* weighted image with a flow compensation from the T2* weighted image without a flow compensation to acquire a third image; and
    producing the vascular image based at least on the third image.

2. The method according to claim 1 wherein an echo time (TE) to apply the first and second readout gradients is more than 15 msec.

3. The method according to claim 1 wherein the first readout gradient is applied in a negative direction and then applied in a positive direction so as to be two times the area of the gradient applied in the negative direction.

4. The method according to claim 1 wherein the second readout gradient is applied in a positive direction in a constant amount, applied two times in a negative direction in the constant amount and then applied in a positive direction so as to be two times the area of the constant amount.

5. The method according to claim 1 wherein the T2* weighted image without a flow compensation is a minimized flow phenomenon image and the T2* weighted image with a flow compensation is a weighted flow phenomenon image.

6. The method according to claim 5, further comprising outputting the minimized flow phenomenon image and the third image or a MIP (Maximum Intensity Projection) image of the third image as the result.

7. The method according to claim 1, wherein the phase without a flow compensation is expressed as the following equation (3):

$$\phi = -\gamma \int_0^{\tau+2\alpha+2\beta} G_0 a_0 dt - \gamma \int_0^{\tau+2\alpha} G_0 a_1 t dt - \gamma \int_{\tau+2\alpha}^{\tau+2\alpha+\beta} \quad \text{[Formula 3]}$$

$$(G_0 - G_r) a_1 t dt - \gamma \int_{\tau+2\alpha+\beta}^{\tau+2\alpha+2\beta} (G_0 + G_r) a_1 t dt$$

$$= -\gamma \left[ G_0 a_0 (\tau + 2\alpha + 2\beta) + G_r a_1 \beta^2 - \frac{1}{2} G_0 a_1 (\tau + 2\alpha + 2\beta)^2 \right].$$

8. The method according to claim 7, wherein the phase with a flow compensation is expressed as the following equation (4):

$$\phi = -\gamma \int_0^{\tau+2\alpha+2\beta} G_0 a_0 dt - \gamma \int_0^{\tau} G_0 a_1 t dt - \gamma \int_{\tau}^{\tau+\alpha} (G_0 + G_r)$$
$$a_1 t dt - \gamma \int_{\tau+\alpha}^{\tau+2\alpha+\beta} (G_0 - G_r) a_1 t dt - \gamma \int_{\tau+2\alpha+\beta}^{\tau+2\alpha+2\beta} (G_0 + G_r)$$
$$a_1 t dt$$

$$= -\gamma \Big[ G_0 a_0 (\tau + 2\alpha + 2\beta) + G_r a_1 (\beta^2 - \alpha^2) - \frac{1}{2} G_0 a_1 (\tau + 2\alpha + 2\beta)^2 \Big].$$

[Formula 4]

9. The method according to claim 1, wherein a certain interval not applied by the readout gradient is comprised between the use of the first readout gradient and the use of the second readout gradient.

10. The method according to claim 1, further comprising the step of performing MIP (Maximum Intensity Projection) on the third image to reconstitute a vascular image.

\* \* \* \* \*